US008187576B2

(12) United States Patent
Bandres et al.

(10) Patent No.: US 8,187,576 B2
(45) Date of Patent: May 29, 2012

(54) PLASTICIZER OF NATURAL ORIGIN FOR NAIL POLISH

(75) Inventors: Matthieu Bandres, Toulouse (FR);
Alain Deswartvaegher, Bidos (FR);
Pascale De Caro, Toulouse (FR);
Jean-Pierre Senet, Buthiers (FR);
Sophie Thiebaud Roux, L'union (FR)

(73) Assignee: Durlin France, Bergerac (FR)

( * ) Notice: Subject to any disclaimer, the term of this patent is extended or adjusted under 35 U.S.C. 154(b) by 534 days.

(21) Appl. No.: 12/160,441

(22) PCT Filed: Jan. 10, 2007

(86) PCT No.: PCT/EP2007/050214
§ 371 (c)(1),
(2), (4) Date: Jul. 10, 2008

(87) PCT Pub. No.: WO2007/080172
PCT Pub. Date: Jul. 19, 2007

(65) Prior Publication Data
US 2010/0158835 A1    Jun. 24, 2010

(30) Foreign Application Priority Data
Jan. 11, 2006    (FR) ..................... 06 00248

(51) Int. Cl.
*A61K 8/00* (2006.01)
*A61Q 3/02* (2006.01)
(52) U.S. Cl. .................... 424/61; 424/78.02; 514/57
(58) Field of Classification Search .................. None
See application file for complete search history.

(56) References Cited

U.S. PATENT DOCUMENTS

| | | | |
|---|---|---|---|
| 3,269,971 A * | 8/1966 | Goldblum | 524/280 |
| 4,318,682 A | 3/1982 | Larson et al. | |
| 4,801,331 A | 1/1989 | Murase | |
| 4,820,509 A | 4/1989 | Yamazaki et al. | |
| 5,066,484 A | 11/1991 | Castrogiovanni et al. | |
| 5,145,670 A | 9/1992 | Castrogiovanni et al. | |
| 5,225,185 A | 7/1993 | Castrogiovanni et al. | |
| 5,227,155 A | 7/1993 | Castrogiovanni et al. | |
| 5,578,297 A | 11/1996 | Mellul et al. | |
| 5,662,891 A | 9/1997 | Martin | |
| 5,882,636 A | 3/1999 | Mui et al. | |
| 6,254,878 B1 * | 7/2001 | Bednarek et al. | 424/401 |
| 6,280,756 B1 | 8/2001 | Ramin et al. | |
| 2003/0152535 A1 | 8/2003 | Malnou et al. | |

FOREIGN PATENT DOCUMENTS

| | | |
|---|---|---|
| FR | 2785531 | 5/2000 |
| FR | 2823108 | 10/2002 |
| FR | 2 842 729 | 1/2004 |
| FR | 2842729 | 1/2004 |
| FR | 2842729 A1 * | 1/2004 |
| JP | 2004-315479 | 11/2004 |
| WO | WO 02/058644 A1 | 8/2002 |
| WO | 03 094870 | 11/2003 |
| WO | WO 03094870 A1 * | 11/2003 |
| WO | WO 2006014831 A1 * | 2/2006 |

OTHER PUBLICATIONS

Machine translation of FR2842729 (Nurit et al.).*
Barry M. Trost, "The Atom Economy—A Search for Synthetic Efficiency", Science, vol. 254, Dec. 6, 1991, pp. 1471-1477.
Paul Anastas, Green Chemistry: Theory and Practice, 1998, Oxford University Press submitting Table of Contents only.
John Andraos, "Unification of Reaction Metrics for Green Chemistry II: Evaluation of Names Organic Reactions and Application to Reaction Discovery", Organic Process Research & Development, vol. 9, No. 4, 2005, pp. 404-431.
Roger A. Sheldon, "Consider the environmental quotient When evaluating alternative routes to a product, both the amount and nature of the waste make a difference.", Chemtech, vol. 24, No. 3, 1994, pp. 38-47.
David J. C. Constables, et al., "Metrics to 'green' chemistry-which are the best?", Green Chemistry, vol. 4, 2002, pp. 521-527.
Paul Anastas, Green Chemistry: Theory and Practice, 1998. Oxford University Press. pp. 21-33 and Table of Contents.

* cited by examiner

*Primary Examiner* — Robert A Wax
*Assistant Examiner* — H. Sarah Park
(74) *Attorney, Agent, or Firm* — Oblon, Spivak, McClelland, Maier & Neustadt, L.L.P.

(57) ABSTRACT

The use of at least one carbonate of natural origin as a plasticizer in a film-forming cosmetic composition comprising, in a physiologically acceptable medium, a film-forming polymer and a solvent medium.

14 Claims, No Drawings

PLASTICIZER OF NATURAL ORIGIN FOR NAIL POLISH

The present invention relates to the use of plasticizers of natural origin in a film-forming cosmetic composition comprising in addition a film-forming polymer, the aforesaid composition being usable notably as a composition for the making up or care of keratinous material such as skin, including lips, nails, the lashes, eyebrows and hair, notably of human beings.

The invention also relates to a method for the making up or care of keratinous material, notably of the nails, of human beings.

Among the primary characteristics which nail polishes must possess, the following may be cited in particular: absence of irritation to the skin and nails; easy application; ability to create a homogeneous, glossy film; fast drying. The polish must also adhere well to the nail surface, be somewhat flexible and possess good impact and friction resistance so as to prevent the film from cracking or peeling. To achieve the latter properties, the nail polish must form a film that is both hard and flexible.

In polishes, plasticizers are the components which improve the flexibility of the film without weakening its physical resistance. These compounds also influence other parameters such as the product's drying time or viscosity, but also adhesion and sheen.

The plasticizers commonly used are phthalate molecules such as dibutyl phthalate, citrate molecules such as acetyl tributyl citrate, glycol ester molecules such as neopentyl glycol ester or propylene glycol ester, glycerol benzoate molecules and finally camphor.

Commonly used plasticizers for nitrocellulose have been eliminated from cosmetic compositions little by little over the past few years. Phthalates were targeted initially when some were demonstrated to be harmful to reproduction as well as carcinogenic. In addition to causing allergies, camphor does not yield polishes with constant characteristics due to its volatility. Lastly, the use of any polymer that can be a source of formaldehyde is to be avoided.

All of these restrictions and recommendations encouraged the cosmetics industry to search for new plasticizers for nitrocellulose that would be less hazardous to human health but that would exhibit suitable properties.

From the perspective of substituting the use of phthalates, U.S. Pat. No. 5,882,636 discloses several plasticizers for nitrocellulose such as the adipates, pentaerythrityl tetrabenzoate and 2,2,4-trimethyl-1,3-pentanediol diisobutyrate. In WO 02/058644, Mui et al. select a group of plasticizers for nitrocellulose comprised of trioctyl trimellitate, butylphthalimide isopropylphthalimide, benzyl benzoate, dioctyl malate and dioctyl sebacate. The company L'Oréal has developed numerous plasticizers for nitrocellulose such as epoxidized oils (U.S. Pat. No. 5,578,297), cross-linked polyesters, fluorinated citrates (FR 2,785,531) and sulfonamides (FR 2,823,108). The company Fiabala has proposed a benzoic acid diester (US 2003/0152535).

Several patents mention the use of glycerol-based plasticizers in their formulation. Thus, Castrogiovanni et al. disclose in U.S. Pat. No. 5,066,484 several formulations containing glycerol esters as plasticizers for nail polishes. The same authors disclose in U.S. Pat. No. 5,145,670 that glycerol triacetates and glycerol trioctanoates are also plasticizers for nitrocellulose. U.S. Pat. Nos. 5,227,155 and 5,225,185 by Castrogiovanni et al. disclose formaldehyde-free formulations and claim the use of glycerol triacetylricinoleate and glycerol tribenzoate as plasticizers. Patent JP 2004-315479 also discloses several plasticizing molecules containing glycerol, namely glycerol diacetomonocaprylate, glycerol diacetomonocaprate, glycerol diacetomonolaurate and glycerol diacetomonooleate.

Mixtures of plasticizers have also been disclosed, for example a mixture of citrate and toluene sulfonamides (U.S. Pat. No. 6,280,756), a mixture of sucrose benzoate and sulfonamide (U.S. Pat. No. 4,820,509) and a mixture of sucrose acetate isobutyrate, butyl benzylbenzoate and glyceryl tribenzoate (U.S. Pat. No. 5,662,891).

The use of glycerol carbonate in a gel-type nail lacquer remover is disclosed in U.S. Pat. No. 4,801,331. Carbonate is used as a cellulose solvent but, however, its use as a plasticizer is not mentioned.

WO 03/094870 discloses nail polishes comprising propylene carbonate as a plasticizer. FR 2,842,729 describes cellulose compositions for nail polish which are comprised of a cellulose film-forming agent in an organic solvent medium comprising between 1 and 84% by weight with respect to the total weight of the composition of an organic carbonate and 1 to 84% by weight with respect to the total weight of the composition of an acetal. The total organic solvent content represents preferably 10% to 85% of the total weight of the composition, even more preferably 45% to 75% of the total weight. Among the carbonates, dimethyl, diethyl, methyl and ethyl carbonates and glycerol monocarbonate can be cited in particular, with dimethyl carbonate being the preferred carbonate and the only one that is exemplified. U.S. Pat. No. 6,254,878 discloses a nail polish composition comprising an organic solvent which may be propylene carbonate.

Carbonates are described as plasticizers for nitrocellulose in industrial polishes likely to undergo mechanical operations carried out under high temperature conditions such as thermoforming, heat sealing and hot rolling.

The inventors sought to use plasticizers in nail polishes other than those commonly used while preserving suitable cosmetic characteristics.

Surprisingly, they found that carbonates of natural origin could be used as plasticizers in nail polish or nail care compositions, without modifying the cosmetic properties of the polish, and that a stable composition, as well as a flexible and glossy film, could be obtained.

The present invention also relates to the use as a plasticizer of at least one carbonate of natural origin selected among the carbonates of formula (1):

$$R_1OCOOR_2 \qquad (1)$$

in which
  $R_1$ and $R_2$ are identical and each represents a —$CH_2$—$CH_2$—$CH$—$(CH_3)_2$ group or a —$(CH_2)_{11}$—$CH_3$ group, or
  $R_1$ and $R_2$ together form an alkyl chain comprising 2 to 3 carbon atoms, the aforesaid carbon atoms carrying one or more hydroxy or hydroxy($C_1$-$C_3$)alkyl groups, in film-forming cosmetic compositions comprising in addition, in a physiologically acceptable medium, at least one film-forming polymer and one solvent medium.

The term ($C_1$-$C_3$)alkyl according to the present invention comprises methyl, ethyl, propyl and isopropyl groups.

In an advantageous embodiment of the invention, the plasticizer is chosen from the group comprising diisoamyl carbonate, dilauryl carbonate and glycerol carbonate.

In an even more advantageous embodiment, the chosen plasticizer is glycerol carbonate.

The physicochemical properties sought for a plasticizer are radically different than, even the opposite of, those sought for a solvent. Indeed, a nail polish solvent must evaporate at room temperature, and thus must have a flash point of less than 30° C. In contrast, a plasticizer must remain in the polish film, and thus must have a flash point quite higher than 30° C. to ensure effective and homogeneous plasticizing over time. Thus, since the flash point of glycerol carbonate is above 200° C., it cannot be used as a solvent.

In the context of the present invention, a "carbonate of natural origin" means a carbonate prepared by the reaction of dimethyl carbonate (DMC) with an alcohol of natural origin. An "alcohol of natural origin" means an alcohol extracted or produced from renewable plant raw materials. A molecule is considered of natural origin insofar as it arises from plant, animal or mineral raw materials that can be transformed by authorized chemical and physical processes. Authorized processes are defined by the certification organization Ecocert S.A.S. and are based on French decree no. 95-354 dated Mar. 30, 1995. The carbonation reaction, used for the preparation of plasticizers according to the invention, is an authorized process. Consequently, carbonates prepared from alcohols arising from plant oils may be regarded as of natural origin.

The carbonates used within the framework of the invention may be prepared by all of the transesterification techniques known to those skilled in the art and described in the literature.

Base-catalyzed, acid-catalyzed, metal-catalyzed and lipase-catalyzed transesterification and transesterification in a supercritical medium may be cited in particular.

According to the invention, dimethyl carbonate transesterification is carried out by base catalysis. This method indeed makes it possible to respond effectively to the criteria of green chemistry.

The syntheses may be performed without solvent and are carried out in heterogeneous phases. At the end of the reaction the catalyst is eliminated from the reaction medium by filtration and thus it can be reused and no aqueous effluent is produced.

The catalysts most used for this type of reaction are sodium hydroxide (NaOH), potassium carbonate ($K_2CO_3$) or sodium methoxide (MeONa). In an advantageous embodiment of the invention, potassium carbonate ($K_2CO_3$) will be preferred.

The concept of "green chemistry" was developed in the United States in the early 1990s with the goal of providing a framework for the prevention of pollution related to chemical activities.

In 1991, the U.S. Environmental Protection Agency launched the first green chemistry research initiative by proposing the following definition: "The goal of green chemistry is the design of chemical products and processes that reduce or eliminate the use and generation of hazardous substances."

Paul Anastas (*Green Chemistry: Theory and Practice*, 1998, Oxford University Press) contributed to the development of the idea of green chemistry and popularized "the twelve principles of green chemistry":

1. Prevent waste
2. Design safer chemicals and products
3. Design less hazardous chemical syntheses
4. The use renewable feedstocks
5. The use catalysts, not stoichiometric reagents
6. Avoid chemical derivatives
7. Maximize atom economy
8. The use safer solvents and reaction conditions
9. Increase energy efficiency
10. Design chemicals and products to degrade after use
11. Analyze in real time to prevent pollution
12. Minimize the potential for accidents The need to evaluate and quantify the "green performance" of chemical reactions made it necessary to adopt "green measuring units." The most cited include:

Atom economy (AE), (Trost, *Science*, 1991, 254, 1471). AE is calculated in the following way, for a reaction of type:

$$A + B \rightarrow C$$

$$\text{Atom economy} = \frac{M_{Product\ C}}{M_A + M_B} \times 100$$

where M is the molecular weight of the given compound.

J. Andraos, in *Unification of Reaction Metrics for Green Chemistry II: Evaluation of named organic reactions and application to reaction discovery*, Organic Process Research & Development, 2005, 9, 149-163, proposed a criterion for determining the cleanliness of a reaction. It relates to the "golden" economy of atoms, in reference to the "golden number" known to mathematicians for centuries. This golden number, generally indicated by the symbol Φ, is equal to $(\sqrt{5}-1)/2 = 0.61803\ldots$. Consequently, Andraos suggested that a reaction would qualify as green only if its AE was greater than 0.618.

Environmental impact factor (E), (Sheldon, *ChemTech*, 1994, 24(3), 38):

$$E\text{-Factor} = \frac{\text{Total Waste (kg)}}{\text{Product Formed (kg)}}$$

Reaction mass efficiency, or RME (Constable et al., *Green Chemistry*, 2002, 4, 521), which expresses the mass percentage of the reagents found in the product. Therefore, for a reaction of type:

$$A + B \rightarrow C$$

$$EMR = \frac{\text{Mass of product } C}{\text{Mass of } A + \text{Mass of } B} \times 100$$

Reaction mass efficiency is a combined unit since in its calculation it takes into account the atom economy, yield and stoichiometry of the reagents. Thus it can be used to demonstrate the cleanliness of a reaction.

Mass productivity:

$$\text{Mass Productivity} = \frac{\text{Mass of product}}{\text{Total mass in a process or in a step of a process}} \times 100$$

This unit is useful in demonstrating the efficiency of a reaction from an economic point of view since it emphasizes the optimal use of resources.

Carbon efficiency (CE): this unit is defined as the percentage of carbon atoms of the reagents that are found in the product. For a reaction of type:

$$A + B \rightarrow \text{Product} + \text{co-product}$$

$$\text{Carbon effectiveness} = \frac{\text{Number of moles of product } A \times \text{number of carbons in product}}{(\text{Moles of } A \times \text{carbons in } A) + (\text{Moles of } B \times \text{carbons in } B)} \times 100$$

Dimethyl carbonate is known to be a methylation, carbonylation and transesterification agent that can efficiently replace common toxic reagents such as methyl halides ($CH_3X$), dimethyl sulfate (DMS) and phosgene ($COCl_2$). It is also an example of a green reagent since it is nontoxic, it is not the source of atmospheric emissions and it can be manufactured according to a clean process, namely the oxycarbonylation of methanol (U.S. Pat. No. 4,318,682).

Dimethyl carbonate is used to replace reagents that are toxic, hazardous, produced by non-ecological, nonselective, methods and that produce difficult to reprocess sub-products.

The synthesis of diisoamyl, dilauryl and glycerol carbonates is carried out by the reaction of DMC with three alcohols, respectively, that arise from plant, thus renewable, raw materials:

isoamyl alcohol: primary component of fusel oil, a residue of ethanol distillation;
dodecanol, or lauryl alcohol: manufactured from the lauryl acid, present in numerous plant oils;
glycerol: arises from the hydrolysis of plant oils, a by-product of biodiesel production.

Isoamyl alcohol is the primary constituent (65-75%) of fusel oil, which is a by-product of the alcoholic industry. Indeed, during the production of ethanol by wheat or corn fermentation, the residue recovered in the distiller during distillation is a mixture primarily comprised of $C_2$ to $C_5$ alcohols.

Dodecanol, or lauryl alcohol, is a raw material arising from oils of plant, mineral or animal origin and is principally used in the detergent industry. In plants, the oil is contained in the hard, woody substance of seeds or kernels and is enclosed in oil-producing cells in the form of small droplets. Plant oils contain approximately 98% triglycerides, which yield glycerol and fatty acids when hydrolyzed. An oil is characterized by its composition; indeed, it is composed of various fatty acids which are present in various proportions. Copra (coconut) and palm oils are highly advantageous because they contain a large proportion of lauryl acid. Performing a reduction reaction with the lauryl acid contained in these oils makes it possible to obtain dodecanol.

Natural glycerol is obtained from triglycerides according to three methods:
transesterification (in biofuel or biodiesel production processes, for example);
hydrolysis;
saponification, a soap manufacturing method.

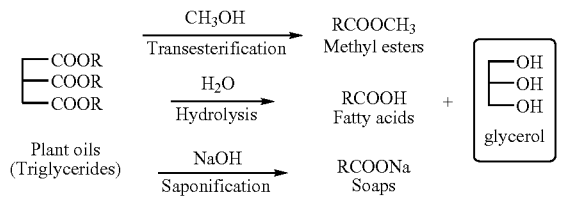

In a highly advantageous embodiment of the invention, at least one compound of formula (1) used as a plasticizer is present in a content ranging from 0.1% to 30% by weight with respect to the total weight of the composition, advantageously from 0.1 to 20%, still more advantageously from 1 to 10%.

Among the film-forming polymers likely to be used, polyurethanes, acrylic polymers, vinyl polymers, polyesters, polyamides and cellulose polymers can be cited in particular.

Advantageously the film-forming polymer is nitrocellulose.

The solvent medium of the organic composition can be an organic solvent medium or an aqueous medium.

As organic solvents that can be used in the invention, the following can be cited:

ketones that are liquid at room temperature, such as methylethylketone, methylisobutylketone, diisobutylketone, isophorone, cyclohexanone or acetone;
alcohols that are liquid at room temperature, such as ethanol, isopropanol, diketone alcohol, 2-butoxyethanol or cyclohexanol;
glycols that are liquid at room temperature, such as ethylene glycol, propylene glycol, pentylene glycol or glycerol;
propylene glycol ethers that are liquid at room temperature, such as propylene glycol monomethyl ether, propylene glycol monomethyl ether acetate or dipropylene glycol mono n-butyl ether;
short-chain esters (having from 3 to 8 carbon atoms in total) such as ethyl acetate, methyl acetate, propyl acetate, n-butyl acetate or isopentyl acetate;
ethers that are liquid at room temperature, such as diethyl ether or dimethyl ether;
alkanes that are liquid at room temperature, such as decane, heptane, dodecane or cyclohexane;
and mixtures thereof.

In an advantageous embodiment of the invention, the organic solvents used are of plant origin. For example, solvents containing esterified fusel oil can be cited, advantageously fusel oils comprised of a mixture of $C_1$-$C_5$ alcohols containing:

0% to 95%, advantageously 30% to 90%, even more advantageously 50% to 80%, of a mixture of 2-methyl-1-butanol, 3-methyl-1-butanol and 1-pentanol;
0.5% to 20%, advantageously 5% to 15%, of a mixture of 1-propanol and 2-propanol; and
2% to 63%, advantageously 10% to 20%, of a mixture of 1-butanol and 2-methyl-1-butanol.

The esterification of this fusel oil leads to a $C_3$-$C_7$ acetate mixture containing:

0% to 95%, advantageously 30% to 90%, even more advantageously 50% to 80%, of a mixture of secondary amyl acetate, isoamyl acetate and n-amyl acetate;
0.5% to 20%, advantageously 5% to 15%, of a mixture of n-propyl acetate and isopropyl acetate; and
2% to 63%, advantageously 10% to 20%, of a mixture of n-butyl acetate and isobutyl acetate.

When the composition according to the invention contains an aqueous medium, the latter may be primarily comprised of water or of a hydroalcoholic mixture notably including $C_1$-$C_5$ monoalcohols or $C_2$-$C_8$ glycols. The water content in the aqueous medium composition can range from 25 to 94.9% by weight with respect to the total weight of the composition, and preferably from 60 to 90% by weight.

The film-forming polymer may be present, in dry matter, in a content ranging from 1 to 60% by weight with respect to the total weight of the composition, better still from 10 to 40% by weight.

The compositions obtained according to the invention can be constituted by, in addition, at least one additive chosen from the group comprised by thickening agents, spreading agents, wetting agents, dispersing agents, anti-foaming agents, preservatives, UV filters, dyes, pigments, active ingredients, surfactants, hydrating agents, fragrances, neutralizers, stabilizers and antioxidants.

The invention also relates to a nail polish comprised of a composition obtained by the use such as previously defined.

The invention also relates to a method for the making up or cosmetic care of keratinous material, notably of the nails, wherein a composition such as previously defined is applied to the keratinous material.

The carbonates used within the framework of the invention may be prepared by all of the transesterification techniques known to those skilled in the art and described in the literature.

Base-catalyzed, acid-catalyzed, metal-catalyzed and lipase-catalyzed transesterification and transesterification in a supercritical medium may be cited in particular.

According to the invention, dimethyl carbonate transesterification is carried out by base catalysis. This method indeed makes it possible to respond effectively to the criteria of green chemistry.

The syntheses may be performed without solvent and are carried out in heterogeneous phases. At the end of the reaction the catalyst is eliminated from the reaction medium by filtration and thus it can be reused and no aqueous effluent is produced.

The catalysts most used for this type of reaction are sodium hydroxide (NaOH), potassium carbonate ($K_2CO_3$) or sodium methoxide (MeONa). In an advantageous embodiment of the invention, potassium carbonate ($K_2CO_3$) will be preferred.

According to the invention, DMC can be made to react with one or two alcohols of natural origin of formula (2):

$R_1OH$ $R_2OH$ (2)

in which
R$_1$ and R$_2$, identical or different, each represent a linear or branched, saturated or unsaturated alkyl group having, independently of each other, 1 to 24 carbon atoms, advantageously from 1 to 12 carbon atoms, even more advantageously from 1 to 5 carbon atoms, the aforesaid alkyl groups optionally being substituted by one or more hydroxy groups,
in the presence of a base catalyst such as potassium carbonate, for example, and without solvent, to obtain a compound of formula (1):

R$_1$OCOOR$_2$ (1)

in which
R$_1$ and R$_2$ are identical and each represents a —CH$_2$—CH$_2$—CH—(CH$_3$)$_2$ group or a —(CH$_2$)$_{11}$—CH$_3$ group, or
R$_1$ and R$_2$ together form an alkyl chain comprising 2 to 3 carbon atoms, the aforesaid carbon atoms carrying one or more hydroxy or hydroxy(C$_1$-C$_3$)alkyl groups.

The reaction can be carried out in the presence of an azeotropic agent such as heptane, for example.

Examples 1 to 5 and FIGS. 1 and 2, which follow, illustrate the preparation of carbonates used according to the invention, the cleanliness of the syntheses and the plasticizing properties of the aforesaid carbonates.

EXAMPLE 1

Synthesis of Diisoamyl Carbonate

The reaction scheme is as follows:

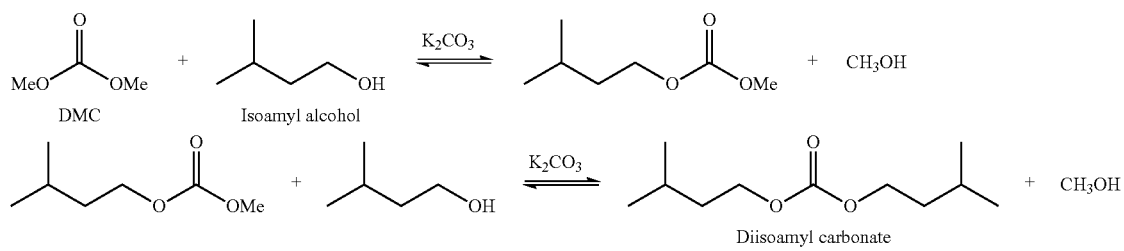

Slightly hydrated (H$_2$O<1%) fusel oil is used as the source of isoamyl alcohol. Isoamyl alcohol/DMC stoichiometry is set at 5:1. Potassium carbonate is introduced in a catalytic quantity equal to 1% (by weight with respect to the DMC).

Heating at 130° C. for 1 h with continuous elimination of the methanol formed makes it possible to achieve a diisoamyl carbonate yield of 75%.

Highly pure diisoamyl carbonate is easily obtained by simple filtration of the solid catalyst followed by distillation under reduced pressure.

EXAMPLE 2

Synthesis of Dilauryl Carbonate

The reaction scheme is as follows:

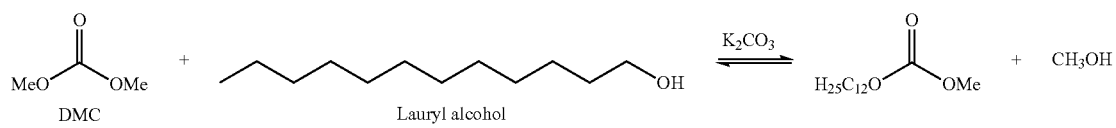

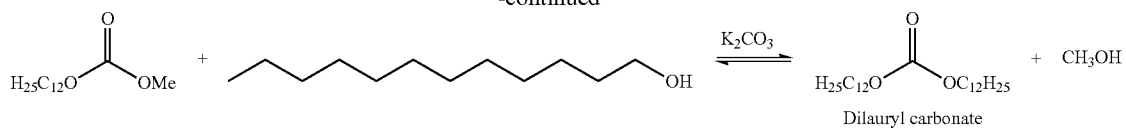

The DMC is reacted with 5 equivalents of dodecanol, in the presence of 1% (by weight with respect to the DMC) potassium carbonate. Heating at 150° C. for 5 h allows the formation of dilauryl carbonate.

The catalyst is removed from the reaction medium by filtration and the unreacted dodecanol is eliminated by distillation under reduced pressure to obtain a dilauryl carbonate yield of 48%.

EXAMPLE 3

Synthesis of Glycerol Carbonate

The reaction scheme is as follows:

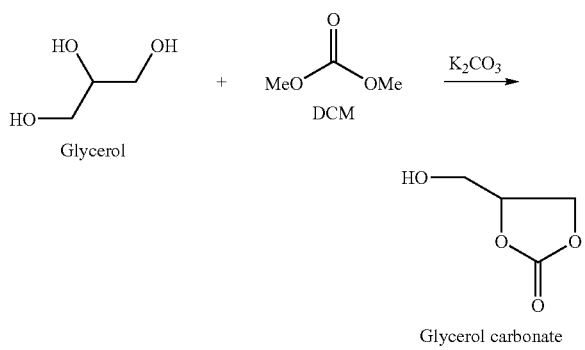

The DMC is reacted with 3 equivalents of glycerol, in the presence of 1% (by weight with respect to the DMC) potassium carbonate. The reaction medium is heated at 75° C. for 3 h, until the glycerol totally disappears.

Since potassium carbonate is soluble when heated in the reaction medium, catalysis is homogeneous in this case. Filtration on a cation-exchange resin (Amberlit IR-120) makes it possible to remove the catalyst from the reaction medium and to obtain a glycerol carbonate yield of 98%. This procedure presents the advantage of avoiding any delicate operation for separating glycerol from glycerol carbonate.

EXAMPLE 4

Evaluation of Carbonate Syntheses Cleanliness

The factors characteristic of green chemistry were evaluated for examples 1 to 3. They are compared with those of a carbonylation method traditionally used in industry, namely phosgenation. As of 2003, phosgene remained the most-used source of carbonyl, accounting for 80% of industrial carbonate preparation. The results are given in table 3 below.

TABLE 3

Syntheses cleanliness

| Example | AE (%) | E-Factor | MP (%) | CE (%) | RME (%) | Ecotoxicity |
|---|---|---|---|---|---|---|
| 1 | 75.9 | 0.32 | 75 | 29 | 28.6 | None |
| 2 | 86.1 | 0.11 | 90 | 19 | 18.7 | None |
| 3 | 64.8 | 0.77 | 56 | 31 | 29.7 | None |
| Phosgenation (Catalyst: pyridine) | 73.5 | 6.1 | 14 | 100 | 66.0 | Formation of HCl; highly toxic reagents |

AE = atom economy
E-Factor = environmental factor
PM = mass productivity
CE = carbon efficiency RME=reaction mass efficiency The desirability of the alcohol carbonation method developed in examples 1 to 3 resides in the very low production of waste (characterized by the E-Factor) and the significant impact on the overall reduction of the reaction's ecotoxicity.

The waste generated by the methods of examples 1 to is constituted by the methanol formed during the reaction and the dimethyl carbonate which is distilled in azeotrope form with methanol during the purification of the reaction medium. This 70:30 (by weight) methanol:DMC azeotropic mixture is not easily recycled. On the other hand, the majority of the DMC initially introduced in excess is distilled with high purity and can be reused in the following batch. It is thus not taken into account in the calculation of the environmental factor.

EXAMPLE 5

Characterization of Plasticizing Capacity

Plasticizing capacity is measured by two techniques:
  DMA (dynamic mechanical analysis) measurements: observation of a reduction in $T_g$;
  Persoz pendulum: damping by the film.

All of the parameters are studied by comparing the properties of a base containing a reference plasticizer, acetyl tributyl citrate, with those of bases containing diisoamyl carbonate, dilauryl carbonate or glycerol carbonate.

5.1. DMA Analyses
5.1.1. Procedure

The glass transition temperature ($T_g$) of the film is measured by DMA (dynamic mechanical analysis).

Glass transition temperature characterizes the mobility of polymer chains. Chains that move easily yield polymers with a low glass transition temperature, whereas chains with reduced mobility yield polymers with a high $T_g$.

Thus, it is perhaps judicious to add a plasticizer to a polymer if said polymer has a $T_g$ that is too high. The plasticizer molecule is placed between the polymer chains and moves them apart from each other, thus increasing free volume.

The plasticizing properties of a molecule can therefore be characterized by the decrease in the glass transition temperature of the polymer studied.

Measurements are carried out on films whose formulation contains diisoamyl carbonate, dilauryl carbonate or glycerol carbonate and are compared with those obtained with a film formulated with a reference plasticizer, acetyl tributyl citrate.

5.1.2. Results

The results are given in the table below.

TABLE

| Formulation | $T_g$ (° C.) |
| --- | --- |
| Clear base without plasticizer | 38.7 |
| Clear base + 5.57% acetyl tributyl citrate | 22.3 |
| Clear base + 5.57% diisoamyl carbonate | 33.5 |
| Clear base + 5.57% dilauryl carbonate | 34.2 |
| Clear base + 5.57% glycerol carbonate | 17.4 |

These results clearly snow the plasticizing effect of carbonates and of acetyl tributyl citrate. The decrease in the glass transition temperature of the clear base is significant when these molecules are added therein. It is also noted that at equal concentrations, the plasticizing effect of glycerol carbonate is greater than that of the reference plasticizer.

The measurement of the glass transition temperature of nitrocellulose by DMA makes it possible to demonstrate the better plasticizing capacity of glycerol carbonate with respect to the reference plasticizer, acetyl tributyl citrate.

5.2. Persoz Hardness 5.2.1. Procedure

Persoz hardness is measured with a Persoz pendulum according to the protocol established by the Applicant which meets ASTM D 4366 and EN ISO 1522 standards.

The oscillations of a standardized pendulum, resting on a ball on the surface to be tested, have a damping time directly proportional to the hardness of said surface.

The efficiency of a plasticizer results in a small number of oscillations, that is to say, a soft film which quickly dampens the pendulum's oscillations.

The comparison between the plasticizers was carried out on a standard composition, using solvents of natural origin.

The standard composition is given in table

TABLE 4

Clear standard composition

| Composition (Grade 25) | Amount (%) |
| --- | --- |
| Isoamyl acetate | 29.45 |
| Ethanol | 29.45 |
| Nitrocellulose E27 Nitrocellulose E24 | 17.9 |
| Plasticizer | 9.9 |
| Polyester resin | 13.3 |
| Total | 100 |

5.2.2 Results

Results are given in table 5 below.

TABLE 5

Evolution of Persoz hardness over time for 4 plasticizers

| | Drying time (min) | | | |
| --- | --- | --- | --- | --- |
| | 30 | 60 | 120 | 240 |
| Plasticizer | Persoz hardness | | | |
| Without plasticizer | 85 | 161 | 225 | 295 |
| Acetyl tributyl citrate | 44 | 75 | 116 | 138 |
| Diisoamyl carbonate | 74 | 109 | 160 | 232 |
| Dilauryl carbonate | 78 | 106 | 151 | 196 |
| Glycerol carbonate | 15 | 26 | 35 | 46 |

The results show the evolution of the hardness of a film over time. Diisoamyl and dilauryl carbonates are plasticizers for nitrocellulose, even if their plasticizing capacity is lower than that of the reference plasticizer. At equal concentrations, the plasticizing capacity of glycerol carbonate appears much higher than that of acetyl tributyl citrate, a synthetic plasticizer used in many nail polish compositions. These results also corroborate the preceding results obtained by dynamic mechanical analysis.

EXAMPLE 6

Formulation of a Nail Polish from Ingredients of Natural Origin

A nail polish has been formulated exclusively from ingredients of plant or mineral origin, in accordance with the standards established by Ecocert®. The properties sought for a nail polish such as drying time, sheen and adherence to the nail are similar to, and even better than, those of a conventional formulation containing products of petrochemical origin.

| Components | Source | Composition |
| --- | --- | --- |
| Isoamyl acetate | Beet fermentation + esterification | 50.7% |
| Ethanol | Beet or cane fermentation | 12.47% |
| Nitrocellulose* | Cotton + nitration | 16.2% |
| Glycerol carbonate | Glycerol + carbonation | 2.5% |
| Alkyd resin | Plant oil + esterification | 12.8% |
| Stearalkonium hectorite | Clay + plant oil | 1.6% |
| Citric acid | Sugar fermentation | 0.03% |
| Natural organic pigments | Plant extracts + grafting on a mineral support | 1.5% |
| Mineral pigments | Mineral oxides | 0.2% |
| Nacre | Mica and mineral oxides | 2% |

*dampened to 70% in ethanol

EXAMPLE 7

Formulation of a Cosmetic Care Composition from Products of Natural Origin

The formulation of a clear composition for cosmetic care application can also be obtained from ingredients of plant origin. Glyceryl laurate was chosen as the active ingredient for its antibacterial, antimicrobial and antifungal properties.

| Components | Source | Composition |
| --- | --- | --- |
| Isoamyl acetate | Beet fermentation + esterification | 54.8% |
| Ethanol | Beet or cane fermentation | 12% |
| Nitrocellulose* | Cotton + nitration | 17% |
| Glycerol carbonate | Glycerol + carbonation | 3% |
| Alkyd resin | Plant oil + esterification | 11.2% |
| Glyceryl laurate | Coconut oil + esterification | 2% |

*dampened to 70% in ethanol

The invention claimed is:

1. A process for producing a film-forming cosmetic composition, said process comprising mixing
glycerol carbonate,
at least one film-forming polymer, and
at least one solvent.

2. The process according to claim 1, wherein the glycerol carbonate is present in a content ranging from 0.1% to 30% by weight with respect to the total weight of the composition.

3. The process according to claim 1, wherein the film-forming polymer is selected from the group consisting of polyurethanes, acrylic polymers, vinyl polymers, polyesters, polyamides and cellulose polymers.

4. The process according to claim 1, wherein the film-forming polymer is nitrocellulose.

5. The process according to claim 1, wherein the solvent is an organic solvent.

6. The process according to claim 1, wherein the solvent is an aqueous solvent.

7. The process according to claim 1, wherein the film-forming polymer is present, in dry matter, in a content ranging from 1% to 60% by weight with respect to the total weight of the composition.

8. The process according to claim 1, wherein the composition includes at least one additive selected from the group consisting of thickening agents, spreading agents, wetting agents, dispersing agents, anti-foaming agents, preservatives, UV filters, dyes, pigments, active ingredients, surfactants, hydrating agents, fragrances, neutralizers, stabilizers and antioxidants.

9. A nail polish comprising a film-forming cosmetic composition obtained by the process of claim 1.

10. A method for coating a keratinous material, comprising applying to the keratinous material a film-forming cosmetic composition obtained by the process of claim 1.

11. The process according to claim 1, wherein the film-forming polymer is selected from the group consisting of polyurethanes, acrylic polymers, vinyl polymers, polyesters and polyamides.

12. The process according to claim 1, wherein the glycerol carbonate is present in a content ranging from 0.1% to 20% by weight with respect to the total weight of the composition.

13. The process according to claim 1, wherein the glycerol carbonate is present in a content ranging from 1% to 10% by weight with respect to the total weight of the composition.

14. The process according to claim 1, wherein the film-forming polymer is present, in dry matter, in a content ranging from 10% to 40% by weight with respect to the total weight of the composition.

* * * * *